(12) United States Patent
Salgo et al.

(10) Patent No.: US 9,089,278 B2
(45) Date of Patent: Jul. 28, 2015

(54) ULTRASONIC ASSESSMENT OF CARDIAC SYNCHRONICITY AND VIABILITY

(75) Inventors: Ivan Salgo, Pelham (MA); Scott Settlemier, Marlborough, MA (US); Peter Chang, Burlington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 629 days.

(21) Appl. No.: 12/997,899

(22) PCT Filed: Jun. 30, 2009

(86) PCT No.: PCT/IB2009/052841
§ 371 (c)(1),
(2), (4) Date: Dec. 14, 2010

(87) PCT Pub. No.: WO2010/004479
PCT Pub. Date: Jan. 14, 2010

(65) Prior Publication Data
US 2011/0098562 A1    Apr. 28, 2011

Related U.S. Application Data

(60) Provisional application No. 61/079,663, filed on Jul. 10, 2008.

(51) Int. Cl.
*A61B 8/00*       (2006.01)
*A61B 8/08*       (2006.01)
(Continued)

(52) U.S. Cl.
CPC .............. *A61B 8/08* (2013.01); *A61B 8/0883* (2013.01); *A61B 8/483* (2013.01); *A61B 8/485* (2013.01); *A61B 8/543* (2013.01); *G01S 7/52042* (2013.01); *G01S 7/52071* (2013.01); *G06T 7/204* (2013.01); *A61B 5/0456* (2013.01); *G01S 15/8993* (2013.01); *G06T 2207/10132* (2013.01); *G06T 2207/30048* (2013.01)

(58) Field of Classification Search
USPC ......................................................... 600/443
See application file for complete search history.

(56) References Cited

U.S. PATENT DOCUMENTS 5,474,073 A    12/1995    Schwartz
5,485,842 A    1/1996    Quistgaard
(Continued)

FOREIGN PATENT DOCUMENTS

EP    1804078 A1    7/2007
JP    2007175235 A    7/2007
(Continued)

*Primary Examiner* — Unsu Jung
*Assistant Examiner* — Saurel J Selkin

(57) ABSTRACT

An ultrasonic imaging system produces a sequence of images of the heart during a cardiac cycle. The images are analyzed to determine the motion, displacement, or change in size of segments of the myocardium. In a preferred embodiment the values determined are radial, longitudinal, or circumferential myocardial strain values. The displacement of the myocardial segments may be tracked during the cardiac cycle by speckle tracking or border detection. The motion, displacement, or change in size values for the segments are analyzed to produce a recruitment curve and anatomical display showing the relative times of recruitment of the different segments in the contractile and relaxation motion of the heart. Participation in and achievement of full recruitment may be determined by comparison against an initial recruitment threshold criterion and against a predetermine maximal recruitment milestone level.

15 Claims, 7 Drawing Sheets

(51) Int. Cl.
  *G01S 7/52* (2006.01)
  *G06T 7/20* (2006.01)
  *A61B 5/0456* (2006.01)
  *G01S 15/89* (2006.01)

(56) References Cited

U.S. PATENT DOCUMENTS

| | | |
|---|---|---|
| 5,720,291 A | 2/1998 | Schwartz |
| 5,833,613 A | 11/1998 | Averkiou |
| 6,013,032 A | 1/2000 | Savord |
| 6,186,950 B1 | 2/2001 | Averkiou |
| 6,352,507 B1 | 3/2002 | Torp et al. |
| 6,375,617 B1 | 4/2002 | Fraser |
| 6,442,289 B1 | 8/2002 | Olsson et al. |
| 6,491,636 B2 | 12/2002 | Chenal |
| 6,692,438 B2 | 2/2004 | Skyba |
| 2002/0072671 A1 * | 6/2002 | Chenal et al. ............... 600/450 |
| 2004/0254486 A1 | 12/2004 | Heimdal |
| 2005/0075567 A1 | 4/2005 | Skyba |
| 2005/0203390 A1 * | 9/2005 | Torp et al. ............... 600/437 |

FOREIGN PATENT DOCUMENTS

| | | |
|---|---|---|
| JP | 2008073423 A | 4/2008 |
| WO | 2007046074 A1 | 4/2007 |
| WO | 2007054861 A1 | 5/2007 |
| WO | 2007107926 A1 | 9/2007 |
| WO | 2007138522 A1 | 12/2007 |

* cited by examiner

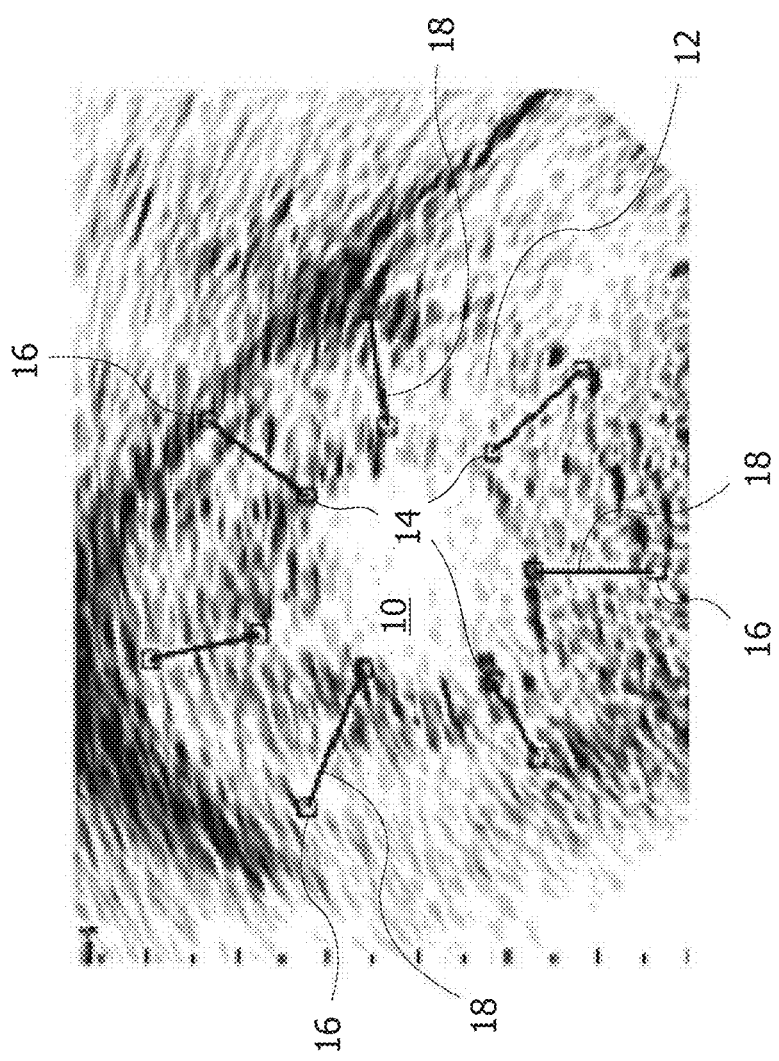

Recruitment Strain Criterion (%): 20
Recruitment Strain Milestone (% max): 85

⦿ Radial Strain Recruitment
○ Circ. Strain Recruitment

ULTRASONIC ASSESSMENT OF CARDIAC SYNCHRONICITY AND VIABILITY

This invention relates to medical diagnostic ultrasound systems and, in particular, to ultrasound systems which perform assessment of synchronicity and viability of cardiac performance.

There exist many ultrasonic methods to assess and quantify cardiac chamber function. Ventricular wall motion indicative of myocardial infarction and ejection fraction are basic diagnostic tools for echocardiographers. These diagnostic tools require that the heart chamber be defined and tracked over a series of images over the cardiac cycle so that measurements of the delineated myocardium and heart chamber can be made. Techniques for delineating the heart wall in an ultrasound image include for example automated border tracking of blood tissue interfaces and tissue Doppler imaging of cardiac wall motion to quantify velocity of contraction, among others. The ability to delineate and track myocardial motion is important for diagnosing the synchronicity of the electrical stimulation of the heart, and also to assess akynetic areas of the heart which can be caused by conditions such as ischemia, hibernation, or stunning. The heart is commanded to contract by electrochemical signals passed by sodium and potassium channels in the muscle cells of the myocardium. These signals, dispersed as they are over the entire heart muscle, should command the heart muscle cells to contract at the same instant in time. When this happens the heart contracts from a relaxed, full volume to a contracted minimal volume, thereby pumping a maximal volume of blood with each heartbeat. This is a characteristic of a healthy heart. However, when the signals that stimulate this contraction cause different regions of the heart to contract at different times, the erratic contraction will pump less than the maximal volume of blood, producing reduced efficiency and taxing the heart over time. It is desirable to be able to diagnose this condition so that the necessary treatment regime, generally the implantation of a pacemaker with leads placed to force synchronous contractions, can be performed if needed. This diagnosis and its treatment are referred to as cardiac resynchronization therapy, or CRT.

A disease condition which can affect electromechanical transduction of the heart is left bundle branch block. Left bundle branch block occurs when transmission of the cardiac electrical impulse is delayed or fails to conduct along the rapidly conducting fibers of the main left bundle branch or in both left anterior and posterior fascicles. This can cause the left ventricle to depolarize slowly via cell-to-cell conduction spreading from the right ventricle to the left ventricle. This condition results in a loss of synchronicity of chamber contraction and a consequent inefficient ejection of blood volume from the chamber. Accordingly, it is desirable to be able to effectively and accurately identify and quantify indications and effects of this loss of synchronicity.

In accordance with the principles of the present invention, the motion or displacement of the myocardium is tracked and measured over some or all of the systolic and/or diastolic phases of the heart cycle. A preferred measure is the distance measurement known as strain. The measurement is made at different regions of the myocardium and a family of curves is produced for the displacement measures of the different regions. The progressive contributions of the different regions to heart contraction during the heart cycle is quantified graphically, numerically, or both in a cardiac assessment referred to by the inventors as "recruitment." The degree of recruitment assessed has been found to correlate with conditions of left bundle branch block and dilated cardiomyopathy.

In the drawings:

FIGS. 3a-3c illustrate three techniques for measuring displacement or strain in an ultrasound image of the myocardium.

Figure 1:
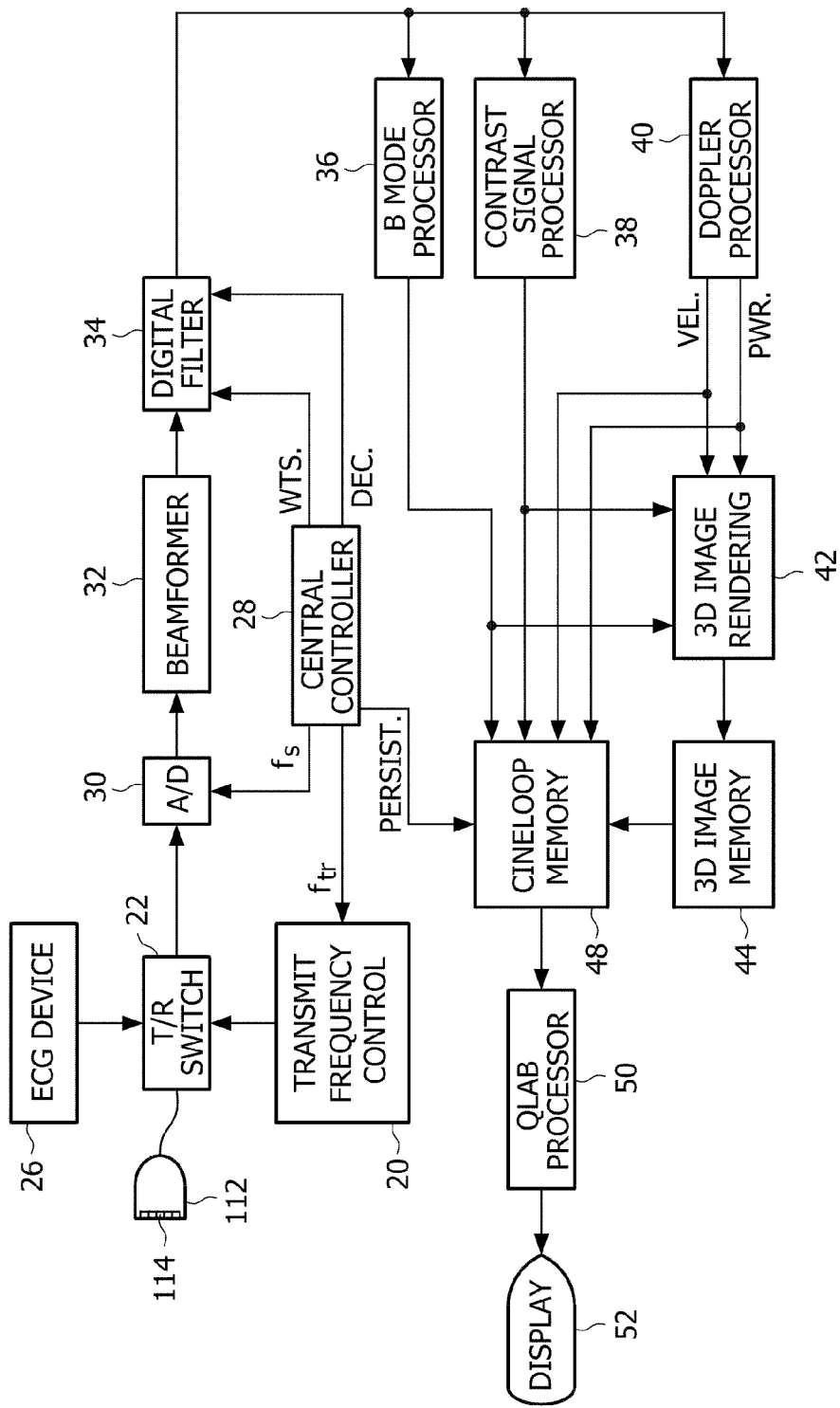
FIG. 1 illustrates in block diagram form an ultrasound system constructed in accordance with the principles of the present invention.

Referring first to FIG. 1 an ultrasonic diagnostic imaging system constructed in accordance with the principles of the present invention is shown in block diagram form. An ultrasonic probe 112 includes an array 114 of ultrasonic transducers that transmit and receive ultrasonic pulses. The array may be a one dimensional linear or curved array for two dimensional imaging, or may be a two dimensional matrix of transducer elements for electronic beam steering in three dimensions. The three dimensional data sets and images described below are preferably acquired using a two dimensional array probe. They may also be acquired with a mechanically swept one dimensional array probe. The ultrasonic transducers in the array 114 transmit ultrasonic energy and receive echoes returned in response to this transmission. A transmit frequency control circuit 20 controls the transmission of ultrasonic energy at a desired frequency or band of frequencies through a transmit/receive ("T/R") switch 22 coupled to the ultrasonic transducers in the array 114. The times at which the transducer array is activated to transmit signals may be synchronized to an internal system clock (not shown), or may be synchronized to a bodily function such as the heart cycle, for which a heart cycle waveform is provided by an ECG device 26. When the heartbeat is at the desired phase of its cycle as determined by the waveform provided by ECG device 26, the probe is commanded to acquire an ultrasonic image. The frequency and bandwidth of the ultrasonic energy generated by the transmit frequency control circuit 20 is controlled by a control signal $f_{tr}$ generated by a central controller 28.

Echoes from the transmitted ultrasonic energy are received by the transducers in the array 114, which generate echo signals that are coupled through the T/R switch 22 and digitized by analog to digital ("A/D") converters 30 when the system uses a digital beamformer. Analog beamformers may also be used. The A/D converters 30 sample the received echo signals at a sampling frequency controlled by a signal $f_s$ generated by the central controller 28. The desired sampling rate dictated by sampling theory is at least twice the highest frequency of the received passband, and might be on the order of at least 30-40 MHz. Sampling rates higher than the minimum requirement are also desirable.

The echo signal samples from the individual transducers in the array 114 are delayed and summed by a beamformer 32 to form coherent echo signals. For 3D imaging with a two dimensional array, it is preferable to partition the beamformer between a microbeamformer located in the probe and the main beamformer in the system mainframe as described in U.S. Pat. No. 6,013,032 (Savord) and U.S. Pat. No. 6,375,617

(Fraser). The digital coherent echo signals are then filtered by a digital filter 34. In this embodiment, the transmit frequency and the receiver frequency are individually controlled so that the beamformer 32 is free to receive a band of frequencies which is different from that of the transmitted band such as a harmonic frequency band. The digital filter 34 bandpass filters the signals, and can also shift the frequency band to a lower or baseband frequency range. The digital filter could be a filter of the type disclosed in U.S. Pat. No. 5,833,613, for example. Filtered echo signals from tissue are coupled from the digital filter 34 to a B mode processor 36 for conventional B mode processing.

Filtered echo signals of a contrast agent, such as microbubbles, are coupled to a contrast signal processor 38. Contrast agents are often used to more clearly delineate the endocardial wall in relation to contrast agent in the blood pool of the heart chamber, or to perform perfusion studies of the microvasculature of the myocardium as described in U.S. Pat. No. 6,692,438 for example. The contrast signal processor 38 preferably separates echoes returned from harmonic contrast agents by the pulse inversion technique, in which echoes resulting from the transmission of multiple pulses to an image location are combined to cancel fundamental signal components and enhance harmonic components. A preferred pulse inversion technique is described in U.S. Pat. No. 6,186,950, for instance.

The filtered echo signals from the digital filter 34 are also coupled to a Doppler processor 40 for conventional Doppler processing to produce velocity and power Doppler signals. The output signals from these processors may be displayed as planar images, and are also coupled to a 3D image processor 42 for the rendering of three dimensional images, which are stored in a 3D image memory 44. Three dimensional rendering may be performed as described in U.S. Pat. No. 5,720,291, and in U.S. Pat. Nos. 5,474,073 and 5,485,842, all of which are incorporated herein by reference.

The signals from the contrast signal processor 38, the B mode processor 36 and the Doppler processor 40, and the three dimensional image signals from the 3D image memory 44 are coupled to a Cineloop® memory 48, which stores image data for each of a large number of ultrasonic images. The image data are preferably stored in the Cineloop memory 48 in sets, with each set of image data corresponding to an image obtained at a respective time. The image data in a data set can be used to display a parametric image showing tissue perfusion at a respective time during the heartbeat. The sets of image data stored in the Cineloop memory 48 may also be stored in a permanent memory device such as a disk drive or digital video recorder for later analysis. In this embodiment the images are also coupled to a QLAB processor 50, where the images are analyzed for recruitment characteristics as described below. The QLAB processor also makes quantified measurements of various aspects of the anatomy in the image and delineates tissue boundaries and borders by automated border tracing as described in U.S. patent publication No. US20050075567 and PCT publication No. 2005/054898. This may be done by fully automated means as described in U.S. Pat. No. 6,491,636, or by assisted automatic border detection as described in the aforementioned U.S. patent publication No. US20050075567. The data and images produced by the QLAB processor are displayed on a display 52.

Figure 2:
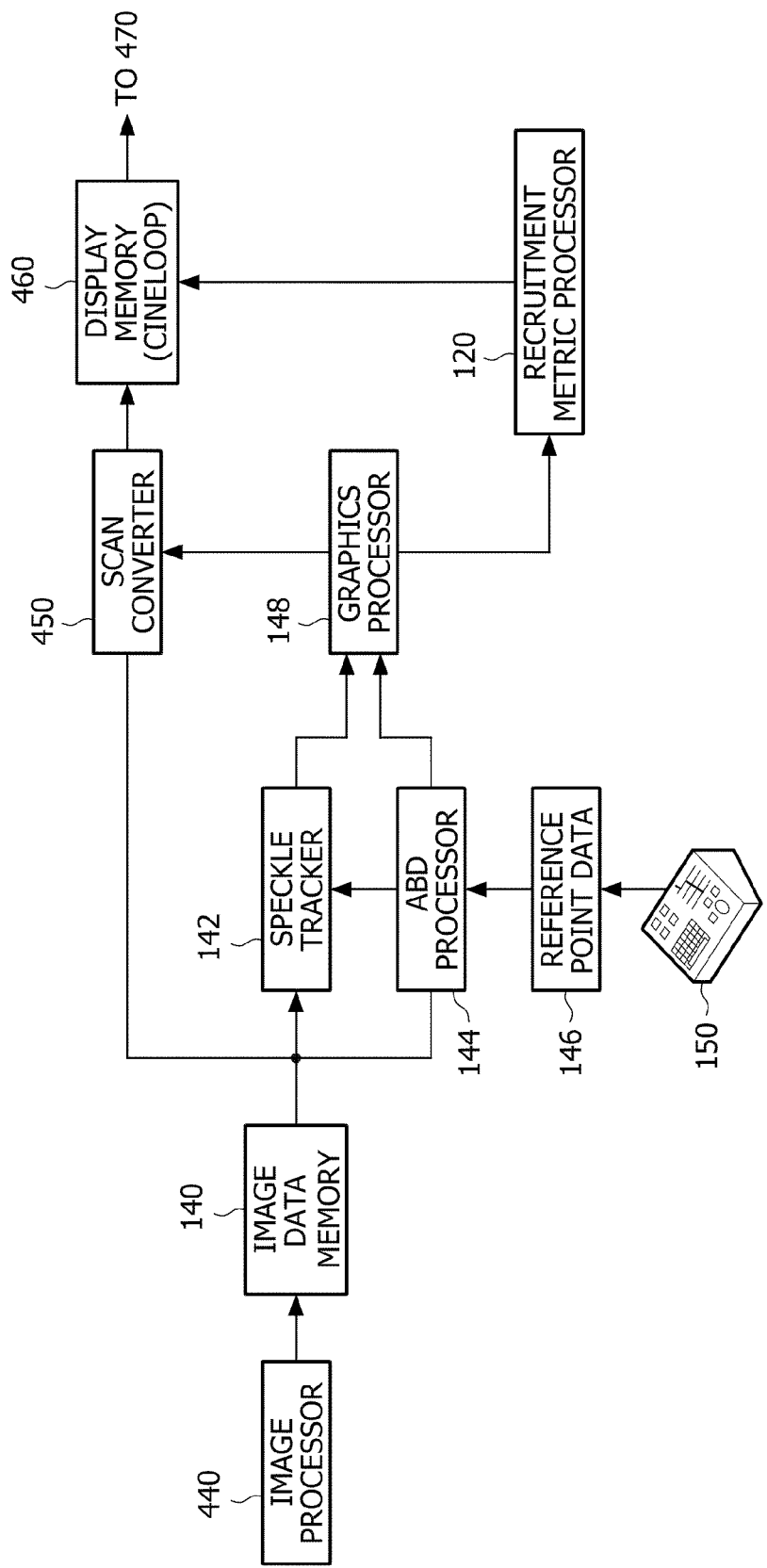
FIG. 2 illustrates the QLab processor portion of the ultrasound system of FIG. 1 in greater detail.

FIG. 2 is a detailed block diagram of the portion of the QLab processor 50 of FIG. 1 when operating in accordance with the present invention. The QLab processor receives images from an image processor 440 such as those preceding the Cineloop memory 48 in FIG. 1. The image processor 440 produces scanline data of an image which is stored in image data memory 140. A first, starting point image of a sequence of heart images is analyzed by border detection of a heart chamber in the image by an ABD processor 144 as described in PCT publication No. 2007/138522. When the border is defined in this first image its location is tracked through subsequent images by a speckle tracker 142, which follows the recurring speckle pattern on or near a delineated tissue border. The initially defined border and the borders in subsequent images are drawn or traced by a graphics processor 148. The ultrasound images of the sequence are converted to the desired display format (e.g., sector, linear, 3D, etc.) by a scan converter 450 which displays the graphically produced borders over the defined border locations in the ultrasound images. The image with its graphic border overlay are stored in a Cineloop memory 460, along with recruitment characteristics produced by a recruitment metric processor 120 which operates on heart images as discussed in detail below. The images and recruitment information are then coupled to the display 52.

Specific points on the identified borders of the successive images are tracked by the speckle tracker 142. which tracks the starting anatomical positions of the points by the speckle pattern produced by the local tissue at the image locations of the points. The speckle tracker 142 identifies regions of pixels around the reference points in the adjacent myocardium. The speckle patterns of these pixels are saved and compared with speckle patterns in the same regions of the successive images and the speckle patterns matched by block matching, as described in U.S. Pat. No. 6,442,289 (Olsson et al.) The difficulty and precision of the matching is determined by establishing a maximum correlation for the matching. The reference point locations in the images are thus tracked from image to image by following the speckle patterns around the points. When the speckle tracker 142 locates the reference points in a new image the reference point locations are coupled to the graphics processor 148, the border redrawn using the newly identified point locations, and a graphic overlay produced for the new image. The new image and its graphic overlay are scan converted and displayed on display 52. The ABD processor 144 may employ the same technique to identify or trace the epicardial border of the myocardium in an image. Further details of the identification of endo- and epi-cardial borders may be found in the aforementioned PCT publication No. 2007/138522.

Instead of tracking the speckle pattern of the myocardial tissue surrounding, underlying, or adjacent to the reference points, it may be appreciated that the reference point locations may be tracked by means other than speckle tracking, that is, by tracking image characteristics which are greater than a wavelength in size. For instance, the movement of specific anatomical features such as the mitral valve plane corners may be tracked. As another example, tissue texture may be tracked. It will also be appreciated that the targeted characteristics may be tracked in either pre-scan converted or post-scan converted image data.

As a final step, the user may want to manually adjust the identified border points or traces so that they precisely outline the border of the underlying myocardium. Located on each identified myocardial border in the example of FIG. 3a are a number of small control points 14,16 as shown in that drawing. The number and spacing of these small control points is a system design choice or may be a variable that the user can set. Using a control on the user interface or control panel 150, the user can point at or near these control points and click and drag the points to more precisely delineate what appears to the user as the myocardial boundary in the image. This process of stretching or dragging the border is known as "rubberbanding", and is described more fully in the aforementioned U.S. Pat. No. 6,491,636, with particular reference to FIG. 9 of that patent. As an alternative to rubberband adjustment, in a more complex embodiment the approximated borders may automatically adjust to the image borders by image processing which uses the intensity information of the pixels at and around the approximated tissue borders. When this process is finished, the control points or border tracing can precisely delineate the boundary of the myocardium in the image.

FIG. 3a illustrates a short axis view cardiac image produced by an ultrasound system constructed in accordance with the principles of the present invention. The heart chamber 10 is shown in the center of the short axis image, surrounded by the myocardium 12. The endocardial and epicardial borders are defined using the techniques described above or those described in U.S. Pat. No. 5,797,396 (Geiser et al.), for instance. A number of control points are defined on both the endo- and epi-cardial borders. Each pair of endo- and epi-cardial control points 14,16 in this example comprises two points positioned at a separate radius of the short axis view. Each pair of control points is joined by a graphically drawn chord line 18 produced by the graphics processor 148 which connects the points. It can be seen that the radial chord lines are all directed at approximately the center of the heart chamber 10. As the myocardium contracts with each heartbeat during systole, the myocardium will move in the direction of the chord lines toward the center of the heart chamber. Correspondingly, when the myocardium relaxes during diastole, the myocardium will move back in the reverse direction. With the control points 14,16 continuing to move with the myocardial borders, the distances between the control points 14,16, that is, the lengths of the chord lines 18, will shorten and lengthen with the contractions of the heart.

In this example the border tracing graphics are not displayed; only the endo- and epi-cardial control points 14,16 and their connecting chords 18 are displayed. In this example the control points for seven lines are positioned around the myocardium and seven chord lines are drawn, although in a given implementation a greater or lesser number of chords can be used or user-defined by means of the user interface 150.

As the sequence of images moves from frame to frame through the cardiac cycle, the endo- and epi-cardial borders will change in relation to each other from image to image as the heart muscle contracts during systole, then relaxes during diastole. One way to quantify this motion or displacement of tissue ultrasonically is the measure known as Lagrangian strain (fractional change in length relative to initial length) or strain rate as described in U.S. Pat. No. 6,537,221 (Criton et al.) Strain is a measure of deformation in tissue and is an indicator of the mechanical effects of muscle tissue. Strain is usually depicted as a dimensionless parameter or percentage, with a change in length as the numerator and the initial length as the denominator of the parameter. Thus the changes in the chord lengths 18 in FIG. 3a from their starting lengths as the heart contract or relaxes can be used to compute a strain measure for each chord line 18 and associated pair of border control points 14,16. Since the chord lines 18 in FIG. 3a are approximately on radii from the center of the heart chamber, these measurements of FIG. 3a are referred to as radial strain.

Figure 3C:
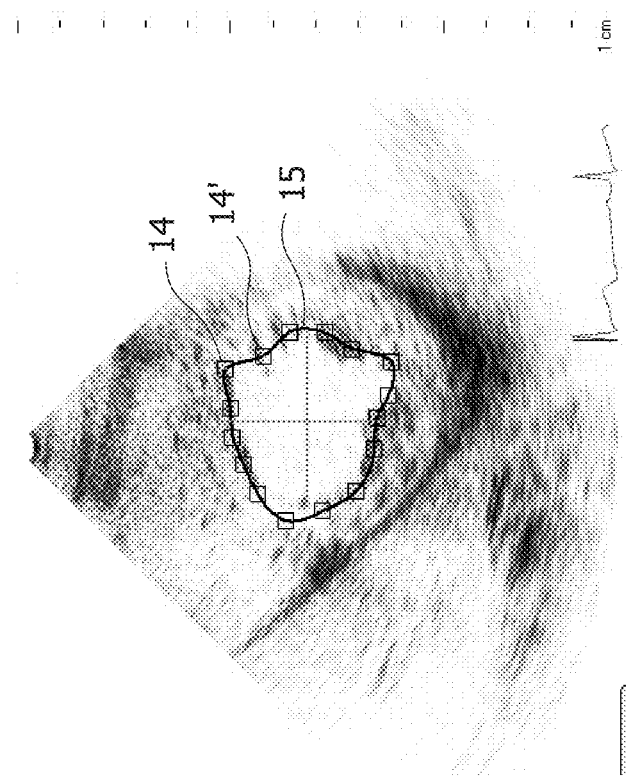
Figure 3B:
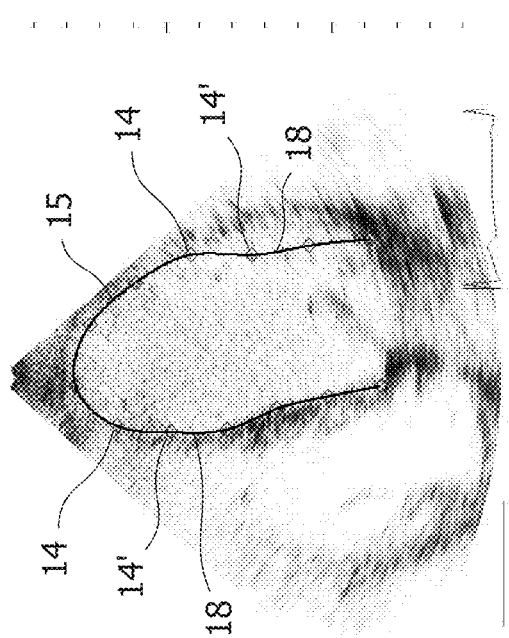

FIG. 3b illustrates a measure of longitudinal strain made along the wall of the heart chamber. In this ultrasound image, a longitudinal cross-sectional view of the left ventricle with an endocardial border tracing 15, control points 14,14' are located around the endocardial border of the heart chamber. Chord lines 18 connect control points 14,14' located along the heart chamber. As the myocardium contracts, the control points 14,14' approach each other and the chord lines 18 between them shorten. Correspondingly, when the myocardium relaxes the adjacent control points draw further apart and the chord lines 18 lengthen. These lengths and length changes can thus be used to make a strain measurement for each chord line.

FIG. 3c illustrates another way to make a strain measurement known as circumferential strain. It is seen that the ABD processor 144 has drawn an endocardial tracing 15 which is drawn along the circumference of the heart wall in this short axis view of the heart chamber. A number of control points 14,14' are located along the border tracing 15. As the heart muscle contracts, the circumferential distance between these control points such as adjacent points 14,14' will decrease. When the heart muscle relaxes, the distance between these points will lengthen again. These displacements can be used to make a measurement of circumferential strain at locations around the endocardial border.

Figure 4:
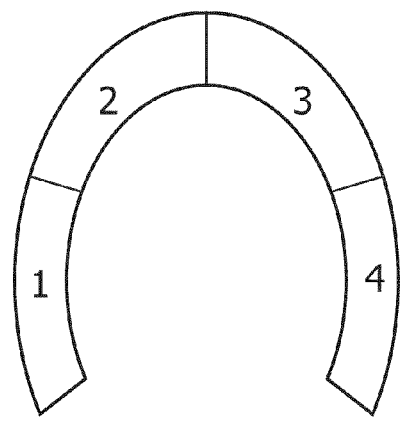
FIG. 4 is a schematic drawing of the segmented myocardial wall of the left ventricle.
Figure 5A:
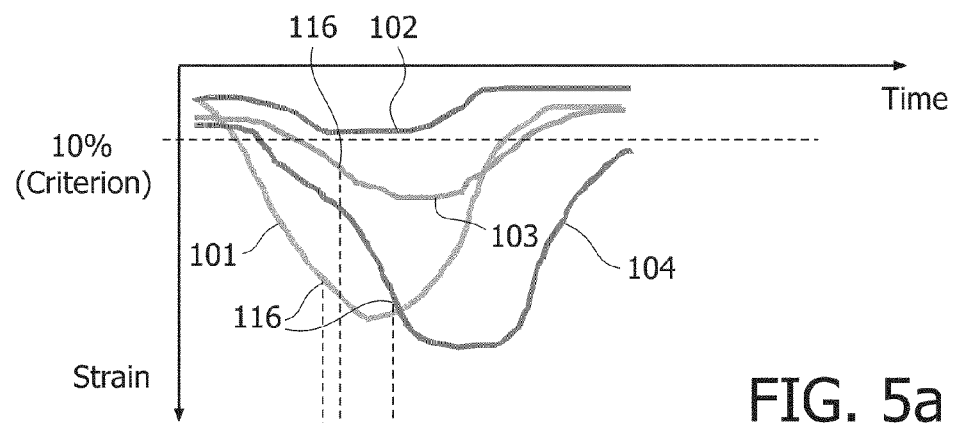
FIGS. 5a and 5b illustrate the production of a recruitment curve in accordance with the principles of the present invention.

In accordance with the principles of the present invention, the strain measurements of myocardial motion or displacement are used to compute a characteristic which the present inventions call "recruitment." The characteristic is so named because it indicates the recruitment or participation in heart displacement or motion by different regions of the heart. Recruitment may be understood with reference to FIGS. 4, 5a and 5b. FIG. 4 is a schematic drawing of the left ventricle (LV) with the apex of the chamber at the top and the mitral valve plane at the bottom. In this example the myocardium of the LV is segmented into four regions identified as 1, 2, 3, and 4. Strain measurements are made over a full heart cycle for each of these myocardial segments and are plotted in FIG. 5a as strain curves 101, 102, 103 and 104, respectively. Each curve reaches its lowest extension when its corresponding segment has moved its maximum distance during myocardial contraction; the curve returns to the top of the plot when the heart relaxes again. It can be seen that the four curves are not moving in unison in this example. That is, the four segments are not synchronized in their movement. Also, it can be seen that various segments have different strain maxima. That is, the displacements of the four segments during a contraction are different. Both of these characteristics are indicated by a recruitment measurement of the present invention.

Figure 5B:
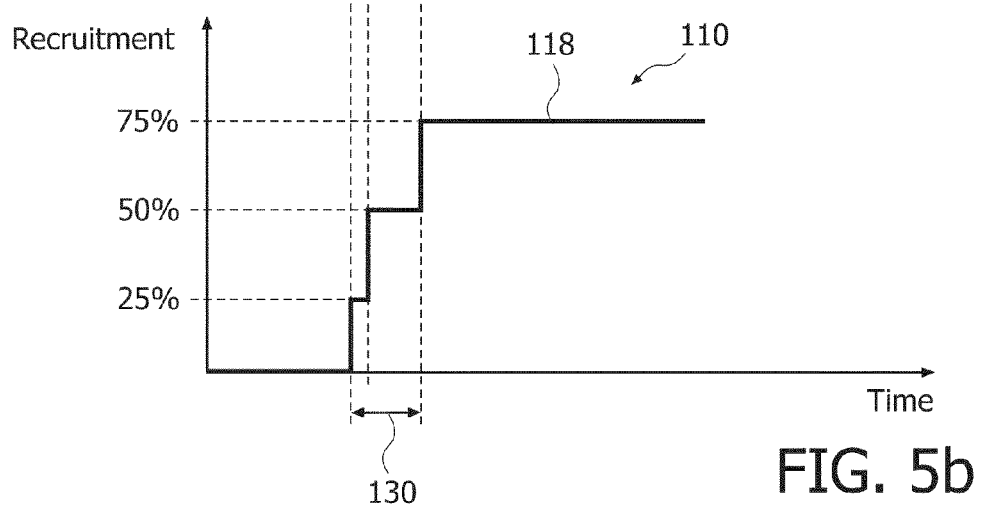

FIG. 5b illustrates a recruitment curve produced in accordance with the present invention. In this example the user first defines a recruitment criterion, which is a threshold strain that a segment must achieve to effectively participate in, or be recruited for, the heart contraction. In this case the user has defined a 10% recruitment criterion indicated by the horizontal dashed line in FIG. 5a. It is seen that curve 102 of myocardial segment 2 does not achieve this threshold criterion. The segment's displacement is insufficient for segment 2 to be recruited for this criterion. The other three curves all cross this criterion and all three are recruited for effective heart contraction in this example.

The user also sets a recruitment milestone level, which is a percentage of the maximum strain of a heart wall segment. The milestone can be set at 100% of a segment's full displacement, or a fraction of the maximum strain measurement. In this example the milestone level is set to 85% of maximum strain. With these parameters defined, the QLab processor 50 can plot a recruitment curve 110 as shown in FIG. 5b. The curve 110 is seen to have a zero starting level prior to heart contraction, and a final plateau level 118 when all recruited segments have achieved the milestone. The steps in the curve 110 show when the segments 1, 3, and 4, represented by curves 101, 103, and 104, have achieved their milestone levels. The milestone level are indicated by 116 and vertical dashed lines are dropped down from these milestones in FIG. 5a. The horizontal dashed lines in FIG. 5b indicate recruitment step levels of 25%, 50%, and 75%, the three steps of the three heart wall segments which are recruited above the 10% criterion. The time taken for the curve 110 to rise from its starting level 116 to its final plateau level 118 is a time duration indicated by arrow 130. The vertical dashed lines between FIGS. 5a and 5b mark the respective times that the strain curves 101-104 reach their 85% milestone levels, which the dashed lines translate down to the recruitment curve. Thus, the rise time duration 130 of the recruitment curve is a measure of the synchronicity of the heart's electrical timing.

If all of the segment curves 101-104 reached their milestone level at the same time, the case for an ideally healthy heart, the recruitment curve 110 would not have multiple steps but would be a single step from the baseline starting level to final level 118, since the segments would be moving in complete synchronism. The duration characteristic indicated by arrow 130 would in that case be zero. Thus, a greater duration indicates poorer synchronicity. The recruitment curve 110 of a healthy heart would also have a number of steps equal to the number of segment curves. That is, all segments of the heart would be recruited for contraction. When a segment is not recruited and is below the recruitment criterion, 10% in this example, the possibility of an infarcted heart wall segment is indicated. Thus, the recruitment curve is sensitive to the extent of the tissue which will eventually be recruited, an ischemia indicator, and is sensitive to how fast tissue will eventually be recruited, which is a synchronicity indicator. Recruitment, therefore, can simultaneously indicate viability and synchronicity. This is important because pacing non-viable tissue is one of the reasons why the CRT procedure fails.

While the preceding example segmented the myocardium into only four segments, it will be appreciated that greater or lesser numbers of segments may alternatively be used, including calculating strain for each pixel. A large number of segments would produce a multitude of steps in the recruitment curve, showing the progressive recruitment of each point of the myocardium to overall heart motion and effectiveness. By color-coding the points in the myocardium, the strain curves, and the steps of the recruitment curve, the times of maximal participation of each point of the myocardium to heart motion may be appreciated.

Figures 6, 7:
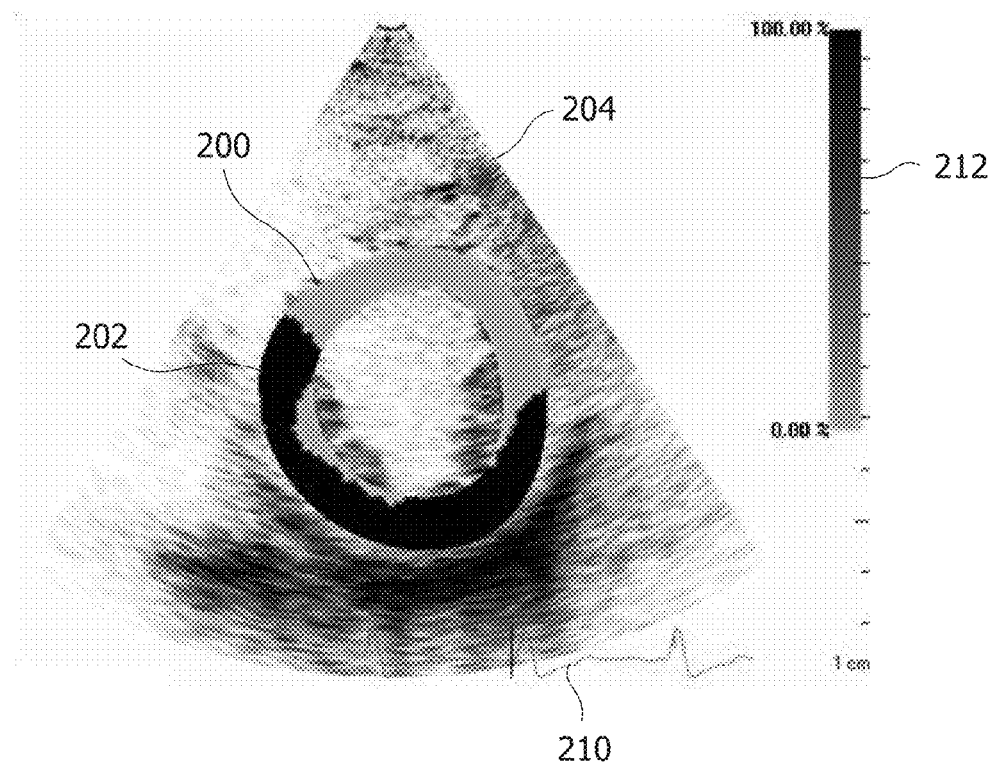
FIG. 6 illustrates a numerical data entry display for the parameters of a recruitment analysis.
FIG. 7 illustrates a parametric image of recruitment.

FIG. 6 illustrates a data entry display box by which a user may set the recruitment curve parameters, criterion and milestone level. In this example the user has set the recruitment strain criterion to 10% and the recruitment strain milestone to 85% of maximum. The circles below these entry points can be set to indicate the use of radial, longitudinal, or circumferential strain measurements for the recruitment analysis.

As an alternative or adjunct to graphical presentation of the recruitment analysis as shown in FIG. 5b, an anatomical parametric display can be used to indicate recruitment as shown in FIG. 7. In this example a circular parametric display band 200 is overlaid over the myocardium shown in an ultrasound image. The cursor on the ECG waveform 210 at the bottom of the display shows the point in the cardiac cycle at which the cardiac image was acquired. The points in the parametric display band 200 are colored to indicate the recruitment of the underlying points of the heart muscle. While progressive recruitment along the strain curve can be indicated by a continuing spectrum of colors or shadings as shown by the color bar 212 to the right of the cardiac image, in this example only a dark and a light color are used to indicate whether the underlying myocardial point has exceeded or not exceeded either the recruitment criterion or the recruitment milestone. A dark shading indicates that the underlying myocardium has been recruited by this phase of the heart cycle, and a light shading indicates that the underlying myocardium has not yet been recruited. The dark region 202 in the lower half of the parametric display band in this example indicates that the myocardial region in the inferior wall has been initially recruited, whereas the region of the myocardium in the anterior wall of the heart, underlying light display band region 204, has yet to be recruited by the time of this phase of the heart cycle.

Figures 8A, 8B, 8C, 8D:
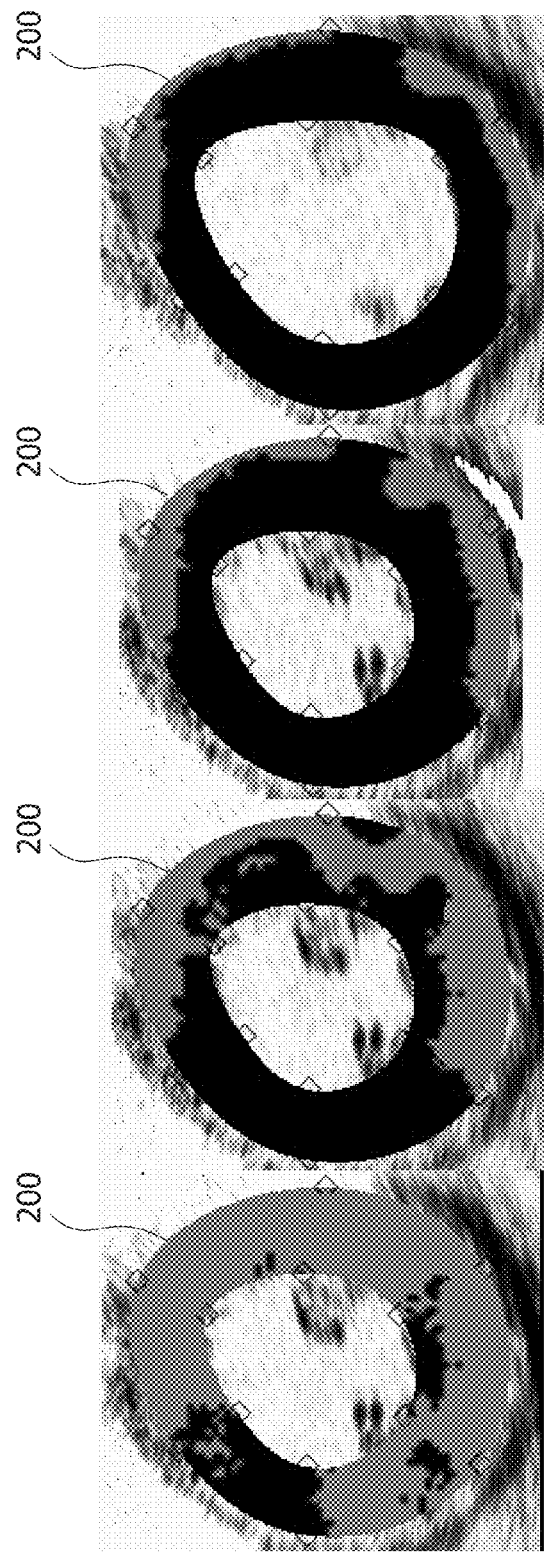
FIGS. 8a-8d illustrate a sequence of parametric images showing the dynamic achievement of a recruitment criterion in accordance with the principles of the present invention.

FIGS. 8a-8d show a series of cardiac images acquired during a heart cycle which indicate the progressive recruitment of regions of the myocardium during the cycle. The dark areas of the parametric display band 200 in FIG. 8a show that initial movement of the heart contract occurs at the upper left (antero-septal) region of the heart in this example. FIG. 8b shows that the left side (septal portion) of the myocardium is now virtually entirely recruited by this phase of the heart cycle, with some movement beginning on the right (lateral) side of the heart. At the time of the heart cycle of FIG. 8c, the entire endocardium and almost the entire right side of the heart are now participating in the contraction, and at the time of the FIG. 8d image recruitment is strongly evident around the full circumference of the heart chamber. A series of images such as those of FIGS. 8a-8d give a clinician a good sense of the synchronicity of the heart contraction and of the times of participation of the different regions of the heart in a contraction.

What is claimed is:

1. An ultrasonic diagnostic imaging system for diagnosing myocardial motion comprising:
   a probe configured to transmit ultrasonic waves into a heart and receives echoes in response;
   an image processor responsive to the echoes and configured to produce a sequence of images of a myocardium over at least a portion of a heart cycle;
   a speckle tracker, responsive to the sequence of images, which is configured to determine motion of a plurality of segments of the myocardium;
   a recruitment processor, responsive to the motion of the segments, which is configured to produce an indicator of cumulative participation of the plurality of segments toward a percentage of a full displacement of the myocardium during the heart cycle and of relative times of participation of the segments in myocardial motion relative to the percentage of full displacement during the heart cycle; and
   a display coupled to the recruitment processor and configured to display the indicator.

2. The ultrasonic diagnostic imaging system of claim 1, wherein the percentage of full displacement is determined by the recruitment processor based on at least one of a minimum recruitment criterion or a recruitment milestone level.

3. The ultrasonic diagnostic imaging system of claim 1, wherein the indicator comprises a graphical recruitment indicator indicating the relative times of recruitment of segments of the myocardium in cardiac contraction.

4. The ultrasonic diagnostic imaging system of claim 1, wherein the indicator comprises a parametric display indicating the relative times of recruitment of segments of the myocardium on an anatomical basis.

5. The ultrasonic diagnostic imaging system of claim 1, wherein the segments correspond to pixels of an ultrasonic image of the myocardium.

6. The ultrasonic diagnostic imaging system of claim 1, wherein the speckle tracker is configured to produce strain values.

7. The ultrasonic diagnostic imaging system of claim 6, wherein the strain values comprise values which are computed as change in length relative to an initial length.

8. The ultrasonic diagnostic imaging system of claim 6, wherein the strain values comprise radial strain values.

9. The ultrasonic diagnostic imaging system of claim 6, wherein the strain values comprise circumferential strain values.

10. The ultrasonic diagnostic imaging system of claim 6, wherein the strain values comprise longitudinal strain values.

11. The ultrasonic diagnostic imaging system of claim 6, wherein the recruitment processor further operates to produce plots of strain values during cardiac contraction for different segments of the myocardium.

12. The ultrasonic diagnostic imaging system of claim 1, wherein the speckle tracker is configured to produce values of tissue displacement.

13. The ultrasonic diagnostic imaging system of claim 1, wherein the speckle tracker is further configured to track the motion of the myocardium by speckle tracking.

14. The ultrasonic diagnostic imaging system of claim 1, wherein the speckle tracker is further configured to track the motion of the myocardium by border detection.

15. The ultrasonic diagnostic imaging system of claim 11, wherein the recruitment processor is further responsive to the strain value plots to produce a recruitment curve for the cardiac contraction.

* * * * *